(12) United States Patent
Hajirahimy

(10) Patent No.: US 7,416,720 B2
(45) Date of Patent: Aug. 26, 2008

(54) TOPICAL AQUEOUS COMPOSITION AS NAIL HARDENER TO DECREASE BRITTLENESS AND INCREASE STRENGTH

(76) Inventor: Morteza Hajirahimy, number 17-second west Koohsar-end Poonak, Tehran (IR) 1477764983

( * ) Notice: Subject to any disclaimer, the term of this patent is extended or adjusted under 35 U.S.C. 154(b) by 332 days.

(21) Appl. No.: 10/940,737

(22) Filed: Sep. 15, 2004

(65) Prior Publication Data

US 2006/0057082 A1  Mar. 16, 2006

(51) Int. Cl.
*A61K 7/42* (2006.01)
*A61K 31/60* (2006.01)

(52) U.S. Cl. .......................................... 424/59; 514/165

(58) Field of Classification Search ................... 424/59, 424/61; 514/165
See application file for complete search history.

(56) References Cited

U.S. PATENT DOCUMENTS 4,767,535 A * 8/1988 Hentschel et al. ...... 210/500.38
5,221,529 A * 6/1993 Tansley ........................ 424/65

FOREIGN PATENT DOCUMENTS

WO  WO 0028958  *  5/2000

* cited by examiner

*Primary Examiner*—Ardin Marschel
*Assistant Examiner*—Zohreh Vakili
(74) *Attorney, Agent, or Firm*—Ide Sazane Aryan; Barry Choobin

(57) ABSTRACT

The present invention is based upon the surprising discovery that the offering aqueous composition according to the invention is capable of being used as topical nail hardener. The present invention relates to a nail hardener that employs a composition of glycerin and water in the preferred concentration as the active components, in a solvent carrier mixture from a group of pharmaceutically acceptable solvents such as ethanol and Propylene glycol.

4 Claims, No Drawings

TOPICAL AQUEOUS COMPOSITION AS NAIL HARDENER TO DECREASE BRITTLENESS AND INCREASE STRENGTH

CROSS-REFERENCE TO RELATED APPLICATIONS

Not applicable

STATEMENT REGARDING FEDERALLY SPONSORED RESEARCH OR DEVELOPMENT

Not applicable

REFERENCE TO SEQUENCE LISTING, A TABLE, OR A COMPUTER PROGRAM LISTING COMPACT DISK APPENDIX

Not applicable

BACKGROUND OF THE INVENTION

The present invention relates to an aqueous topical composition that includes Glycerine and water and is used as nail hardener to decrease brittleness and increase strength.

In some healthy people nails are brittle and or soft. Brittle nails break into layers anywhere along free edge. This will result in losing it's beauty. Meanwhile the resulting space will be a suitable place for microorganism's growth. Soft nails break from anywhere along free edge and don't have desired hardness and strength.

Different products have employed various types of compositions. Some of them add a film of different compositions with various thickness and color so improving the strength by increasing the thickness and some other mechanisms. Meanwhile using some colors can cover the area that has the problem.

U.S. Pat. No. 4,267,852 discloses a method and composition for enhancing the growth and strength of fingernails and toenails including the application of a protein-containing composition directly to the nails, followed by the application of a coating of silicon cream and lacquer containing nylon fibers.

U.S. Pat. No. 4,157,095 discloses the use of a fiberglass sheet as a base for an artificial nail. The artificial nail is glued to the nail with acrylic resin, and a final coat of acrylic resin is applied to the artificial nail.

Other fabrics, such as flax, linen and silk are applied to human nails with adhesives and hardeners, to create artificial nails, as disclosed in U.S. Pat. No. 4,627,453.

Those products has been efficient in many cases, But the need still exists for an improved composition for hardening nails. The present invention can be washed by water so does not leave any layer.

BRIEF SUMMARY OF THE INVENTION

The present invention is based upon the surprising discovery that the offering composition according to the invention is capable of being used as nail hardener to decrease brittleness and increase strength.

The present invention relates to an aqueous topical composition that contains Glycerin and water in the preferred concentration as the active components, in a solvent carrier mixture from a group of pharmaceutically acceptable solvents such as ethanol and propylene glycol.

These and other aspects of the invention will become apparent to those skilled in the art in light of the specification and claims that follow.

BRIEF DESCRIPTION OF THE SEVERAL VIEWS OF THE DRAWING

Not applicable

DETAILED DESCRIPTION OF THE INVENTION

As discussed above an aqueous topical composition according to the present invention include an active component in a solvent mixture. All the components are widely available commercially and well known and, thus, will not be described in too details here.

The key ingredient in the active component is a mixture of Glycerin and water in a specific ratio. Both are well recognized in the art.

Glycerin (glycerol; 1,2,3-propanetriol) is a mild astringent that causes increased blood flow to the skin. It also allows the propylene glycol to carry better some elements and the like into the epidermis if wanted. The possible mechanism that it helps in this invention is coming soon.

A solvent mixture is employed which preferably includes the following components:

Propylene glycol (1,2-propanediol; methylene glycol) is a moisturizer and produces a pleasant emollient feel when applied to the skin. It also carries some element and active components to skin if desired. Propylene glycol has the additional benefit of being a mild germicide. However, in excessive concentrations the germicidal properties can irritate sensitive facial skin.

Ethanol is the most important solvent in this composition. It has a surfactant property and helps Glycerin and water to be spread and cover all over the nail equally. Ethanol evaporates soon and leaves Glycerin and water to contact the entire nail directly and equally, so they can do their effects well. It is also a good solvent for some additives.

Other suitable solvents for use in the solvent mixture are other alcohols and denatured alcohols, polyethylene glycols and the like. They will be used depending some other specific purposes e.g. to help add effectively some minerals, vitamins, essences and the like.

Each of the components, e.g., propylene glycol, glycerin, and ethanol are generally recognized as safe for topical application to the skin or for cosmetic purposes. The preferred solvent mixture comprises propylene glycol in the range of about 3-5% by volume, Ethanol in the range of 5 3-70% by volume.

The present inventive composition can be employed for purposes including:
1. Preventing brittle nails in otherwise healthy people
   a) From breaking into layers.
   b) From splitting anywhere in the edge
   c) From breaking from the besides
2. Preventing soft nails from splitting anywhere in the edge
3. Making soft nails harder and strengthening them The most preferable formulation is as the table below:

| Material | Percentage in the formulation | --- | Role |
|---|---|---|---|
| Glycerine | 20-30 | By volume | Active |
| Water | 10-17 | By volume | Active |

-continued

| Material | Percentage in the formulation | --- | Role |
| --- | --- | --- | --- |
| Propylene glycol | 3-5 | By volume | Solvent |
| Additives | 0-5 | By volume | Other |
| Ethanol | 53-70 (Up to 100) | By volume | Solvent |

In preparing the composition, Glycerin is mixed with water while gently stirring. Propylene glycol is added now. Then ethanol is added, stirring gently until to make sure it is homogeneous.

The present invention is very simple to prepare but very effective. The possible mechanism is as the following. The major role in the composition is done by Glycerin and water. If the nail is dry the composition increases nail's humidity. If the nail is more humid than it should be, the composition decreases nail's water content. So nails will get the optimum humidity in which they are the most flexible. And they will not break easily. Because they can transfer and scatter external forces that are forced to them and there will be no force accumulation. The mentioned humidity will be got in nails by the offered ratio of Glycerin and water.

In addition, an effective amount of a coloring agent can be added to the composition to make a pleasing color to the product. Furthermore, fragrance can also be added to create a pleasant smell, which can help mask undesired ethanol odor. These materials can be introduced together with, or separately in different stages of preparing the composition based on their physicochemical properties. Some additives such as vitamins, moisturizing oils, minerals, nutrients and the like can also be included. These additives are individually recognized in the art. Meanwhile new additives with different properties always come out by time, which they can also be added if wanted. It should be noted that such components are optional and they are not necessary for the claimed properties of the present invention and will be added only if desired.

Although the preferred compositions and method have been described above, it should be understood that various substitutions, omissions, alternations and modifications may come to mind to those skilled in the art to which this invention pertains. Therefore, it is to be understood that the invention is not to be limited to the specific embodiment disclosed and that modifications and other embodiments are intended to be included within the scope of the appended claims. Although specific terms are employed herein, they are used in a generic and descriptive sense only and not for purposes of limitation.

EXAMPLES

The following examples describe specific aspects of the invention to illustrate the invention and provide a more complete description of the invention for those skilled in the art. The examples should not be construed as limiting the invention, as the examples merely provide specific methodology useful in the understanding and practice of the invention and its various aspects.

Example 1

Preparation of 100 Litters of the Invention

The following describes a suitable method for preparing a composition of the present invention with a preferable concentration. 20 litters of glycerol are mixed with 17 litters of water while gently stirring in normal temperature (20 to 35 C) for about 45 minutes. 3 litters of Propylene glycol are added and stirred for about 45 minutes. Then 60 litters of ethanol are added, stirring gently until for about one hour to have a homogeneous final product.

Example 2

The safety of the topically administered invention is obvious. The components of the invention have been widely used for years in cosmetics and food industries for many purposes. So they are well known to those skilled in the art, and no side effects have been reported in the recommended concentrations.

Example 3

In the first set of experiments, the solution was given to 13 volunteers (between 20 and 42 years old) complaining of nail brittleness and or softness to be administered topically every 12 hours. They were visited daily to be asked about their nails. The nails were also assessed, both visually and via instrumentation by study technicians. After two months 92% were satisfied with the invention. They experienced less brittleness and softness.

Example 4

7 women (between 21 and 35 years old) had chronic problems with their nails tearing and ripping. They used the invention for two months and were observed to have no fingernail tears after 4 weeks of application of the solution. They remarked that their nails looked healthier and more beautiful.

Example 5

In the second set of experiments with different volunteers, 44 people (between 21 and 43 years old) were divided into two equal groups. The invention was applied to one group while in the other group nail was treated with the placebo and used as a control. No one was aware that which solution is the placebo. Nails were treated daily for four weeks, and they were daily visited. In 86% of people applying the invention, significant decrease in brittleness and softness were notified. This ratio was 0.09% in the people applying the placebo.

I claim:

1. A topical aqueous composition for human nails to increase strength and decrease brittleness consisting of:
 (i) Glycerin 20% of the entire composition by volume;
 (ii) Water 17% of the entire composition by volume;
 (iii) Propylene Glycol 3% of the entire composition by volume;
 (iv) Ethanol: 60% of the entire composition by volume.

2. A method of making composition of a topical aqueous solution consisting of:
 (a) Mixing components that are the active ingredients in hardening nails consisting of:
  (i) Glycerin 20% of the entire composition by volume;
  (ii) Water 17% of the entire composition by volume;
  (iii) Propylene Glycol 3% of the entire composition by volume;
 (b) Adding a solvent carrier mixture from a group pharmaceutically acceptable solvents consisting of:
  (iv) Ethanol: 60% of the entire composition by volume.

3. A topical aqueous composition for human nails to increase strength and decrease brittleness consisting of:

(i) Glycerin 20% of the entire composition by volume;
(ii) Water 10% of the entire composition by volume;
(iii) Ethanol: 60% of the entire composition by volume.

4. A method of making composition of a topical aqueous solution consisting of:
   (a) Mixing components that are the active ingredients in hardening nails consisting of:
      (i) Glycerin 20% of the entire composition by volume;
      (ii) Water 17% of the entire composition by volume;
   (b) Adding a solvent carrier mixture from a group pharmaceutically acceptable solvents consisting of:
      (iii) Ethanol: 70% of the entire composition by volume.

* * * * *